United States Patent
Ozawa et al.

(10) Patent No.: US 8,624,966 B2
(45) Date of Patent: Jan. 7, 2014

(54) ENDOSCOPE APPARATUS CALIBRATION WITH COLOR CORRECTION TABLE

(75) Inventors: Satoshi Ozawa, Kanagawa (JP); Takayuki Iida, Kanagawa (JP)

(73) Assignee: Fujifilm Corporation, Tokyo (JP)

(*) Notice: Subject to any disclaimer, the term of this patent is extended or adjusted under 35 U.S.C. 154(b) by 486 days.

(21) Appl. No.: 12/888,785

(22) Filed: Sep. 23, 2010

(65) Prior Publication Data

US 2011/0069162 A1 Mar. 24, 2011

(30) Foreign Application Priority Data

Sep. 24, 2009 (JP) ................ P2009-219244

(51) Int. Cl.
*A61B 1/04* (2006.01)

(52) U.S. Cl.
USPC ............................................. 348/68

(58) Field of Classification Search
USPC ............................................. 348/68
See application file for complete search history.

(56) References Cited

U.S. PATENT DOCUMENTS

| | | | |
|---|---|---|---|
| 4,827,908 A | 5/1989 | Matsuo | |
| 2002/0016620 A1* | 2/2002 | Tsujita | 607/88 |
| 2005/0119527 A1 | 6/2005 | Banik et al. | |
| 2007/0142707 A1 | 6/2007 | Wiklof et al. | |
| 2007/0211274 A1* | 9/2007 | Donomae | 358/1.9 |
| 2009/0054957 A1* | 2/2009 | Shanbaky | 607/89 |
| 2009/0062617 A1 | 3/2009 | Mizuyoshi | |
| 2009/0167149 A1 | 7/2009 | Ito | |
| 2009/0221872 A1 | 9/2009 | Liddle et al. | |
| 2010/0048993 A1* | 2/2010 | Shidara | 600/109 |

FOREIGN PATENT DOCUMENTS

| | | |
|---|---|---|
| EP | 1 672 754 A2 | 6/2006 |
| EP | 1 884 183 A1 | 2/2008 |
| JP | 63-240824 A | 10/1988 |
| JP | 2000-342533 A | 12/2000 |
| JP | 2004-121549 A | 4/2004 |
| JP | 2009-056248 A | 3/2009 |
| JP | 2009-153712 A | 7/2009 |
| WO | WO 2008/115547 A1 | 9/2008 |

OTHER PUBLICATIONS

Japanese Office Action dated Mar. 19, 2013 with a partial English translation.

* cited by examiner

*Primary Examiner* — Richard Torrente
(74) *Attorney, Agent, or Firm* — McGinn IP Law Group, PLLC (57) ABSTRACT

An endoscope apparatus includes: an endoscope which includes an imaging optical system and an illumination optical system; and a control unit which includes light source units and connected to the endoscope and supplying at least excitation light to the illumination optical system, and an image processing section correcting an image signal output from the imaging element on the basis of a predetermined color correction table. The control unit performs a calibration process in such a manner that an image of a color chart having a plurality of color patches with known chromaticity values is captured by an imaging element, chromaticity for each of the plurality of color patches is obtained from an imaging signal of the color chart, and the contents of the color correction table are changed.

12 Claims, 11 Drawing Sheets

ENDOSCOPE APPARATUS CALIBRATION WITH COLOR CORRECTION TABLE

The present application claims priority from Japanese Patent Application No. 2009-219244 filed on Sep. 24, 2009, the entire content of which is incorporated herein by reference.

BACKGROUND OF INVENTION

1. Field of the Invention

The present invention relates to an endoscope apparatus.

2. Description of the Related Art

In an endoscope apparatus for obtaining an endoscope image of the inside of a body cavity by emitting illumination light thereto, an electronic endoscope is used which includes an image capturing means for capturing an image of an object by using returning light (including fluorescence or the like) obtained after emitting illumination light from a light source device and guiding the light to the inside of the body cavity. Then, the endoscope image is displayed on an observation monitor by performing a signal process on an imaging signal obtained from the image capturing means by using a processor, and an observation position such as an affected portion is observed.

Since the diagnosis and operation using the endoscope apparatus are performed on the basis of the observation image displayed on the observation monitor, it is necessary to faithfully reproduce the color of the observation image in order to perform the accurate diagnosis and operation. Accordingly, in this kind of endoscope apparatus, in order to correct a variation in tone caused by an individual difference such as a difference in sensitivity of a solid-state imaging element, an individual characteristic information is stored in the endoscope or the processor, and the individual characteristic information is read out at an appropriate timing so as to adjust a color (JP-A-2000-342533).

However, although original parameters of the apparatus are measured and stored in advance, the values of the parameters may not be equal to the actual characteristics of the apparatus due to a variation in the passage of time, and the appropriate color adjustment is not necessarily performed in some cases.

SUMMARY OF INVENTION

An object of the invention is to provide an endoscope apparatus capable of obtaining a captured image having a satisfactory color balance at all times without storing individual characteristic information.

The present invention has the following configuration.

(1) An endoscope apparatus including: an endoscope which includes an imaging optical system having an imaging element and an illumination optical system having an illumination window, the optical systems being provided at a front end of an endoscope insertion unit inserted into a body cavity; and a control unit which includes a light source unit connected to the endoscope and supplying at least excitation light to the illumination optical system so as to emit light from a fluorescent substance, and an image processing section correcting an image signal output from the imaging element on a basis of a predetermined color correction table and outputting a result thereof, wherein the control unit performs a calibration process that an image of a color chart having a plurality of color patches with known chromaticity values is captured by the imaging element, chromaticity for each of the plurality of color patches is obtained from an imaging signal of the color chart so as to be used as a measured chromaticity value, and contents of the color correction table are changed so that the measured chromaticity value of each of the color patches is equal to the known chromaticity value.

According to the endoscope apparatus of the invention, it is possible to obtain a captured image having a satisfactory color balance at all times.

DESCRIPTION OF EXEMPLARY EMBODIMENTS

Hereinafter, an embodiment of the invention will be described with reference to the accompanying drawings.

Figure 1:
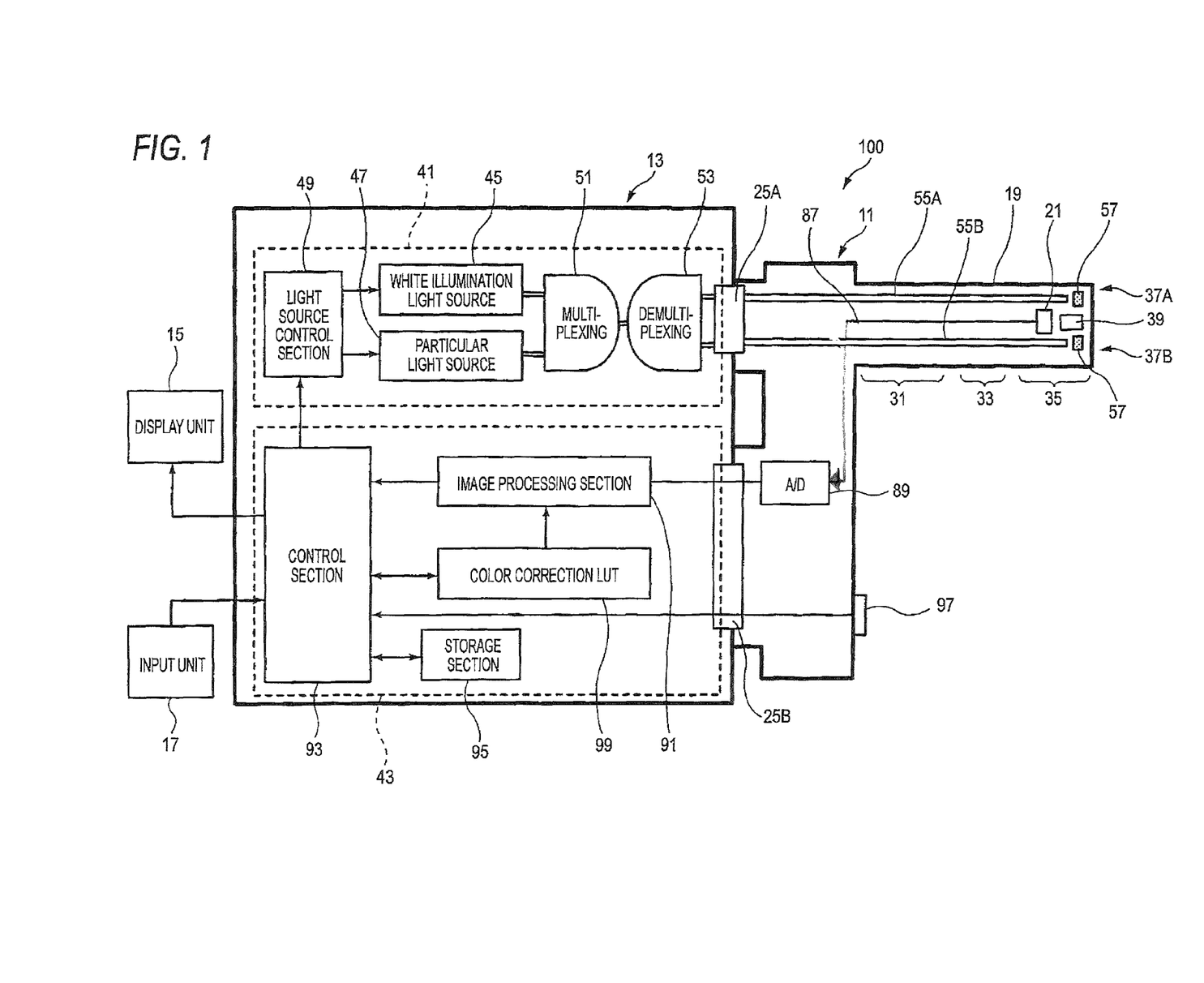
FIG. 1 is a diagram illustrating an embodiment of the present invention, and is a conceptual block diagram of an endoscope apparatus.
Figure 2:
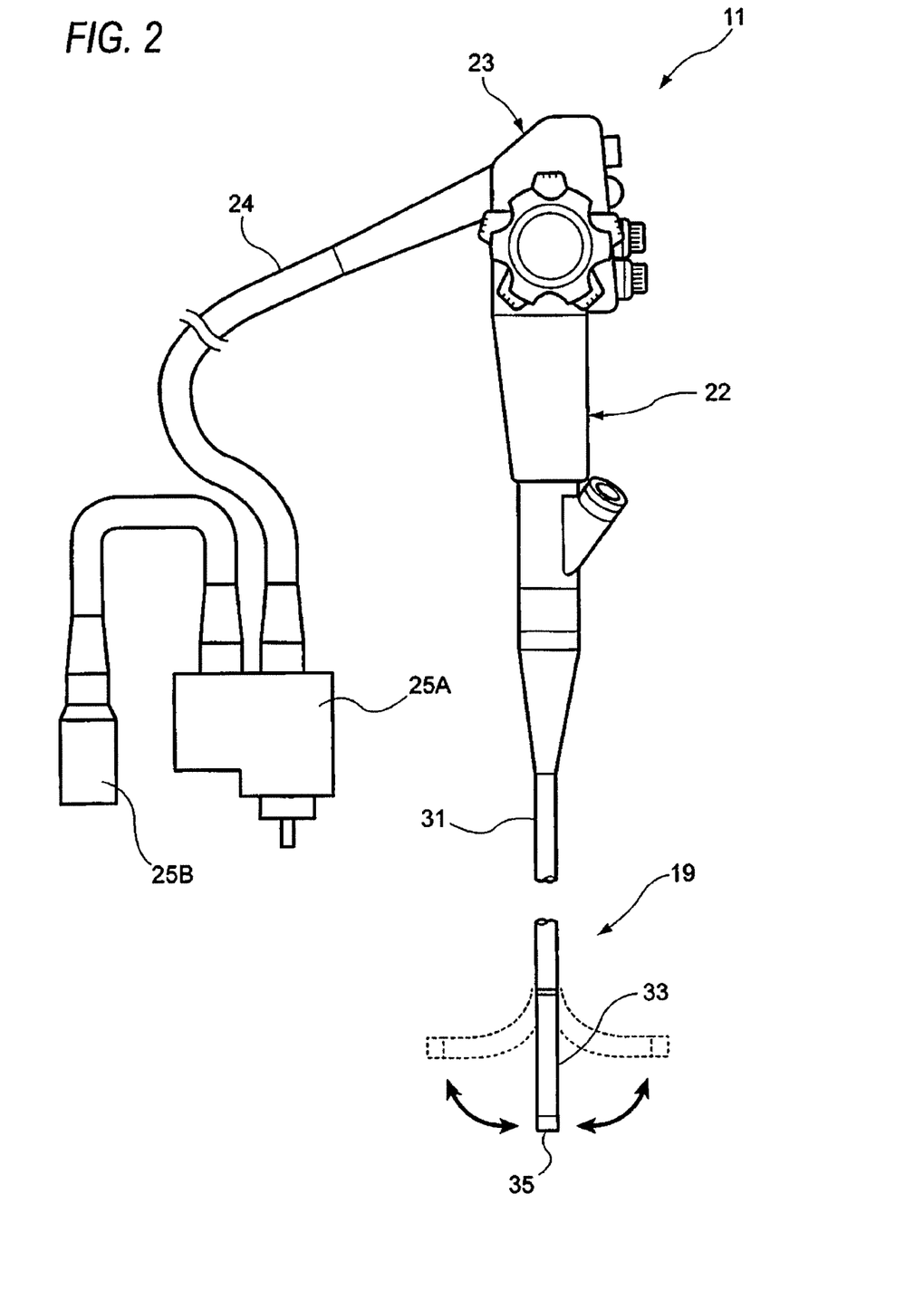
FIG. 2 is an external view as an example of the endoscope apparatus shown in FIG. 1.

FIG. 1 is a diagram illustrating an embodiment of the invention, and is a conceptual block diagram of an endoscope apparatus. FIG. 2 is an external view of an example of the endoscope apparatus shown in FIG. 1.

As shown in FIGS. 1 and 2, an endoscope apparatus 100 includes an endoscope 11, and a control device 13 to which the endoscope 11 is connected. The control device 13 is connected to a display unit 15 which displays image information or the like, and an input unit 17 which receives an input operation. The endoscope 11 is an electronic endoscope which includes an illumination optical system emitting an illumination light from a front end of an endoscope insertion unit 19 and an imaging optical system including an imaging element 21 (refer to FIG. 1) configured to capture an image of an observation area.

In addition, the endoscope 11 includes the endoscope insertion unit 19 which is inserted into a test object, an operation unit 23 (refer to FIG. 2) which is used for an operation of curving the front end of the endoscope insertion unit 19 or an observation operation while being connected to the endoscope insertion unit 19 via an extension portion 22, and connectors 25A and 25B which are used to attachably/detachably connect the endoscope 11 to the control device 13 and are connected to the front end of a universal cable 24. In addition, although not shown in the drawings, the inside of the operation unit 23 and the endoscope insertion unit 19 is provided with various channels such as a clamp channel used for inserting a tissue pickup treatment tool or the like therethrough or an air/water feeding channel.

The endoscope insertion unit 19 includes a flexible portion 31 which has flexibility, a curved portion 33, and a front end portion (hereinafter, referred to as an endoscope front end portion) 35. As shown in FIG. 1, the endoscope front end portion 35 is provided with illumination ports 37A and 37B which are used to emit a light to the observation area, and an imaging sensor 21 such as a CCD (Charge Coupled Device) image sensor or a CMOS (Complementary Metal-Oxide Semiconductor) image sensor which is used to acquire image information of the observation area. The light receiving surface of the imaging element 21 is provided with an object lens unit 39.

The curved portion 33 is provided between the flexible portion 31 and the front end portion 35, and is adapted to be curved by a rotation operation of an angle knob 22 disposed in the operation unit 23. The curved portion 33 may be curved to an arbitrary direction and an arbitrary angle in accordance with a portion of the test object examined by the endoscope 11. The observation direction of the illumination ports 37A and 37B and the imaging element 21 of the endoscope front end portion 35 may be directed to a desired observation portion. In addition, although not shown in the drawings, the illumination ports 37A and 37B of the endoscope insertion unit 19 are provided with a cover glass or a lens.

The control device 13 includes a light source device 41 which generates an illumination light supplied to the illumination ports 37A and 37B of the endoscope front end portion 35, and a processor 43 which performs an image process on an image signal from the imaging element 21, and is connected to the endoscope 11 via the connectors 25A and 25B. In addition, the processor 43 is connected to the display unit 15 and the input unit 17 which are described above. The processor 43 performs an image process on an imaging signal transmitted from the endoscope 11 on the basis of the command from the operation unit 23 of the endoscope 11 or the input unit 17 thereof, and generates and supplies a display image to the display unit 15.

The light source device 41 includes a blue laser light source (white illumination light source) 45 having a central wavelength of 445 nm, and a violet laser light source (particular light source) 47 having a central wavelength of 405 nm. The light emission from each of the semiconductor light emitting elements of the light sources 45 and 47 is individually controlled by the light source control section 49, and the light amount ratio between the light emitted from the blue laser light source 45 and the light emitted from the violet laser light source 47 is changeable.

The blue laser light source 45 and the violet laser light source 47 may use an InGaN-based laser diode of a broad area type, and also may use an InGaNAs-based laser diode or a GaNAs-based laser diode. In addition, as the above-described light source, a light emitting member such as a light emitting diode may be used.

The laser lights emitted from the light sources 45 and 47 are respectively input to optical fibers by a condensing lens (not shown), and are propagated to the connector 25A via a combiner 51 as a multiplexer and a coupler 53 as a demultiplexer. In addition, the invention is not limited thereto, but has a configuration in which the laser lights emitted from the light sources 45 and 47 are directly supplied to the connector 25A without using the combiner 51 and the coupler 53.

The blue laser light having a central wavelength of 445 nm and the violet laser light having a central wavelength of 405 nm are multiplexed, and the laser light propagated to the connector 25A is propagated to the endoscope front end portion 35 of the endoscope 11 by the optical fibers 55A and 55B. Then, the blue laser light excites a fluorescent substance 57 which is a wavelength changing member disposed in the light emitting ends of the optical fibers 55A and 55B of the endoscope front end portion 35 so as to emit fluorescence therefrom. Further, a part of the blue laser light directly transmits the fluorescent substance 57. The violet laser light transmits the fluorescent substance 57 without excitation thereof, and becomes illumination light of a narrow band of wavelength. The fluorescent substances 57 are disposed at each of both sides of the observation window of the imaging element 21, so that it is difficult for a shade to be formed in an object illuminated by the illumination light.

The optical fibers 55A and 55B are multi-mode fibers. As an example, a thin fiber cable may be used which has a core diameter of 105 μm, a cladding diameter of 125 μm, and a diameter of Φ0.3 to 0.5 mm including a protection layer as an outer surface.

The fluorescent substance 57 includes plural types of fluorescent substances (for example, a YAG-based fluorescent substance or a fluorescent substance such as BAM ($BaMgAl_{10}O_{17}$)) which absorbs a part of the blue laser light and is excited to emit light as green to yellow. Accordingly, the blue laser light is changed to white (color similar to white) illumination light by mixing green to yellow excitation light as excitation light with the blue laser light not absorbed and transmitted by the fluorescent substance 57. Like the example of the configuration, when the semiconductor light emitting elements are used as an excitation light source, it is possible to obtain white light having high light emission efficiency and high intensity. Also, it is possible to easily control the intensity of the white light, and to minimally suppress a variation in the color temperature and chromaticity value of the white light.

The fluorescent substance 57 may prevent an occurrence of flickering when performing a video display or overlapping of noise as a barrier in the image capturing operation due to a speckle generated by coherence of laser light. In addition, in the fluorescent substance 57, in consideration of a difference in the refractive index between the fluorescent material forming the fluorescent substance and a fixing/solidifying resin as a filling agent, it is desirable that the particles of the filling agents and the fluorescent material are formed of a material having large scattering and small absorption with respect to the infrared light. Accordingly, it is possible to improve the scattering effect without reducing the light intensity with respect to the light of red or infrared region, and to reduce the optical loss.

Figure 3:
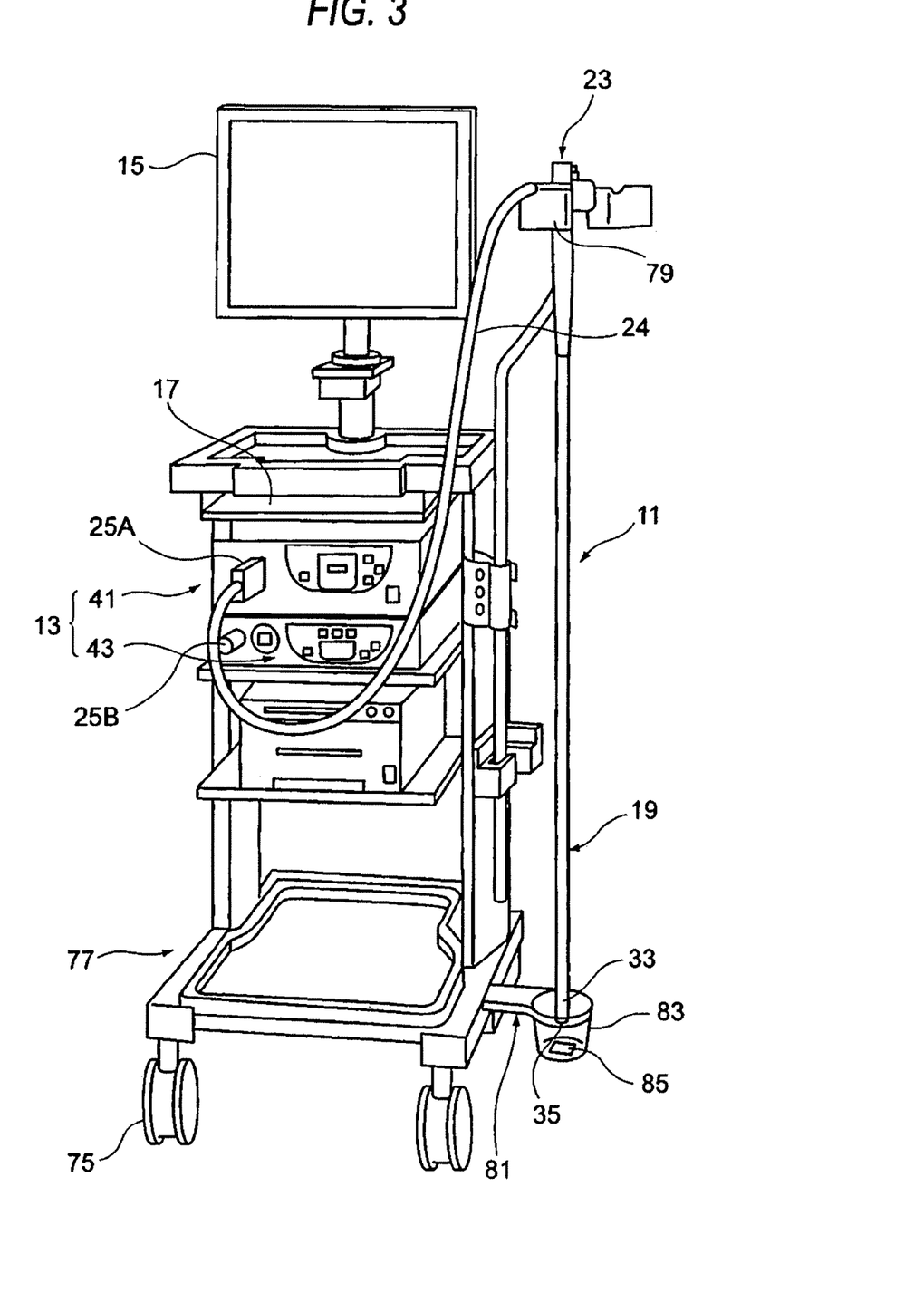
FIG. 3 is an external view of the endoscope apparatus.

FIG. 3 is an external view of the endoscope apparatus.

The light source unit 41, the processor 43, the display unit 15, and the input unit 17 are accommodated in a cart unit 77 having a caster 75 at the lower portion thereof. Likewise, the cart unit 77 mounted with the peripheral devices of the endoscope 11 is provided with an endoscope support port 79 which is used to suspend the operation unit 23 of the endoscope thereon. In the endoscope 11 supported by the endoscope support unit 79, the endoscope insertion unit 19 is drooped at the same position at all times. A base portion 81 of the cart unit 77 is disposed at the lower position extended from of the front end portion 35 of the drooped endoscope insertion unit 19, and a bottomed cylindrical body 83 is fixed to the base portion 81. In the endoscope insertion unit 19 supported by the endoscope support unit 79, the front end portion 35 is inserted into the bottomed cylindrical body 83. In addition, the bottom portion of the bottomed cylindrical body 83 is provided with a color chart 85 which includes a plurality of color patches to be described later in detail.

Returning to FIG. 1, the image signal of the captured image output from the imaging element 21 after the image capturing operation is transmitted to an A/D converter 89 via a signal cable 87, and is converted into a digital signal. The image signal converted into the digital signal is input to an image processing section 91 of the processor 43 via the connector 25B. The image processing section 91 performs various pre-stage processes such as contour emphasis on the captured image signal obtained from the imaging element 21 and converted into the digital signal by the A/D converter 89. Then, the captured image signal subjected to the pre-stage process is divided into the respective captured image signals such as an R signal, a G signal, and a B signal, and is subjected to a color correction process on the basis of the information of the color correction lookup table (color correction LUT) 99 to be described later. The captured image signal subjected to the color correction is then converted into video signals such as a video composite signal and a Y/C division signal, and is output to the control section 93 in the form of desired output image information.

The output image information input to the control section 93 is displayed on the display unit 15 in the form of an endoscope observation image, and is stored in a storage section 95 including a memory or a storage device, if necessary. In addition, the endoscope 11 is provided with a power switch 97, and a start signal is input from the power switch 97 to the control section 93.

In the endoscope apparatus 100 with the above-described configuration, a calibration process is performed in such a manner that the image of the color chart 85 is captured, and the contents of the above-described color correction table 99 are changed on the basis of the color detection result. Hereinafter, the calibration process will be described in detail.

Figure 4:
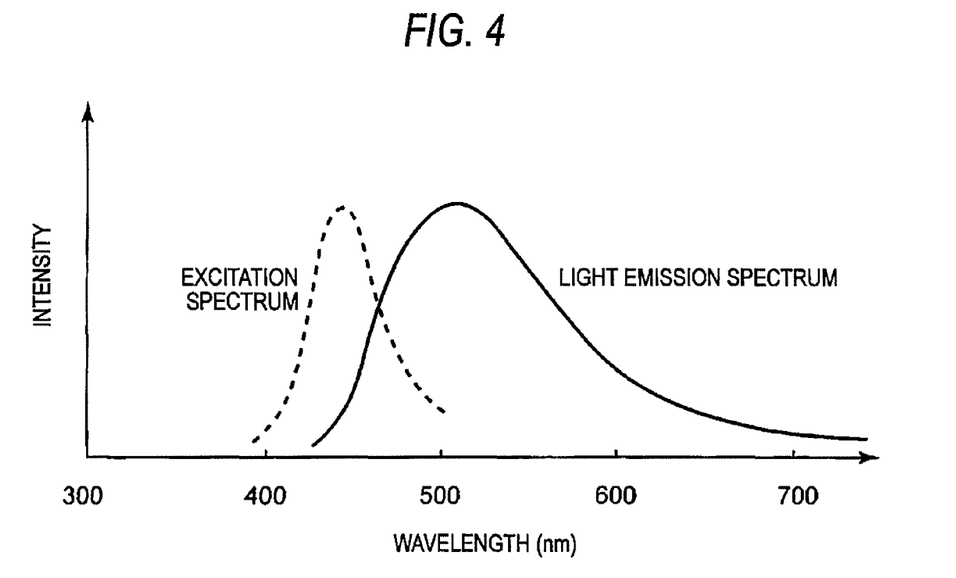
FIG. 4 is a graph showing a relationship between an excitation spectrum and a light emission spectrum.

FIG. 4 is a graph showing an example of an excitation spectrum and a light emission spectrum of the fluorescent substance. In the fluorescent substance of this case, the excitation spectrum depicted by the dotted line absorbs the light within the wavelength bandwidth of 420 to 470 nm, and is allowed to highly efficiently absorb the light of the wavelength of particularly 445 nm. The fluorescent substance 57 is excited by the absorbed excitation light, and emits fluorescence of the spectrum shown as the light emission spectrum depicted by the solid line.

Figure 5:
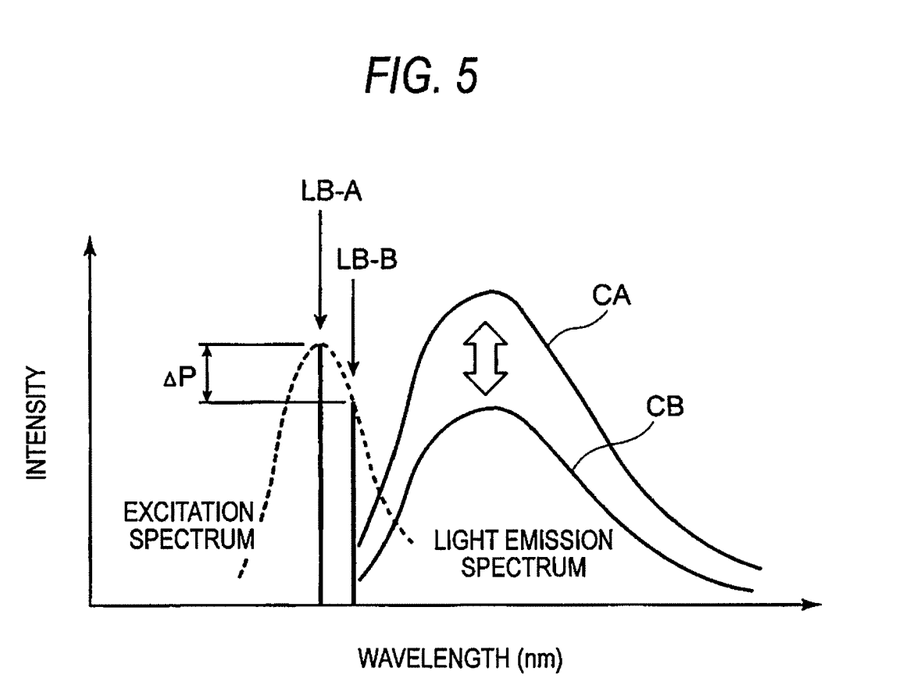
FIG. 5 is an explanatory diagram showing a light emission intensity of a fluorescent substance changing in accordance with the magnitude of absorbed energy.

The light emission intensity of the fluorescent substance 57 is changed in accordance with the magnitude of the absorbed energy. For example, as shown in FIG. 5, if it is assumed that the light emission wavelength of the blue laser light source is deviated by the individual difference or the like, in the case of the laser light LB-A of the stipulated wavelength of 445 nm, the highly efficient absorption occurs at the wavelength at which the excitation spectrum substantially becomes a peak. However, in the case of the laser light LB-B, since the light emission wavelength is deviated, the magnitude of the excitation spectrum is reduced by $\Delta P$. Then, in the LB-B, the light intensity is the same as that of the LB-A, and the light emission spectrum of the fluorescent substance is reduced from CA to CB, thereby causing a relative difference in the light emission intensity of the fluorescent substance.

Then, in the white light formed by the light emission of the fluorescent substance and the blue laser light, the tone of the white light is changed due to a variation in the intensity balance and the light emission (a variation caused by the wavelength) of the fluorescent substance and the blue laser light (constant intensity). That is, in the case where the light wavelength is deviated as in the above-described LB-B, the intensity ratio of the blue laser light relatively increases due to a decrease in the light emission intensity of the fluorescent substance, thereby forming the bluish white light.

Accordingly, in the endoscope apparatus with this configuration, a plurality of laser light sources is used, and the laser lights emitted from them are multiplexed, thereby reducing an influence caused by an individual difference in the wavelength of the light emitted from each of the laser light sources. By multiplexing the lights emitted from the plurality of laser light sources, it is possible to set the central wavelength of the multiplexed laser light to be close to the average wavelength of the respective laser light sources, that is, the stipulated wavelength (445 nm). However, in the endoscope apparatus 100, even when a color is adjusted on the particular endoscope 11 by the combination of the wavelength of the laser light source and the fluorescent substance, if there is a difference in the characteristic of the fluorescent substance when another endoscope is connected, the tone of the illumination light formed by the laser light is changed.

In addition, a variation occurs in the tone of the captured image even by an individual difference of the spectral sensitivity characteristic of the imaging element 21 mounted to the endoscope 11.

Figure 6:
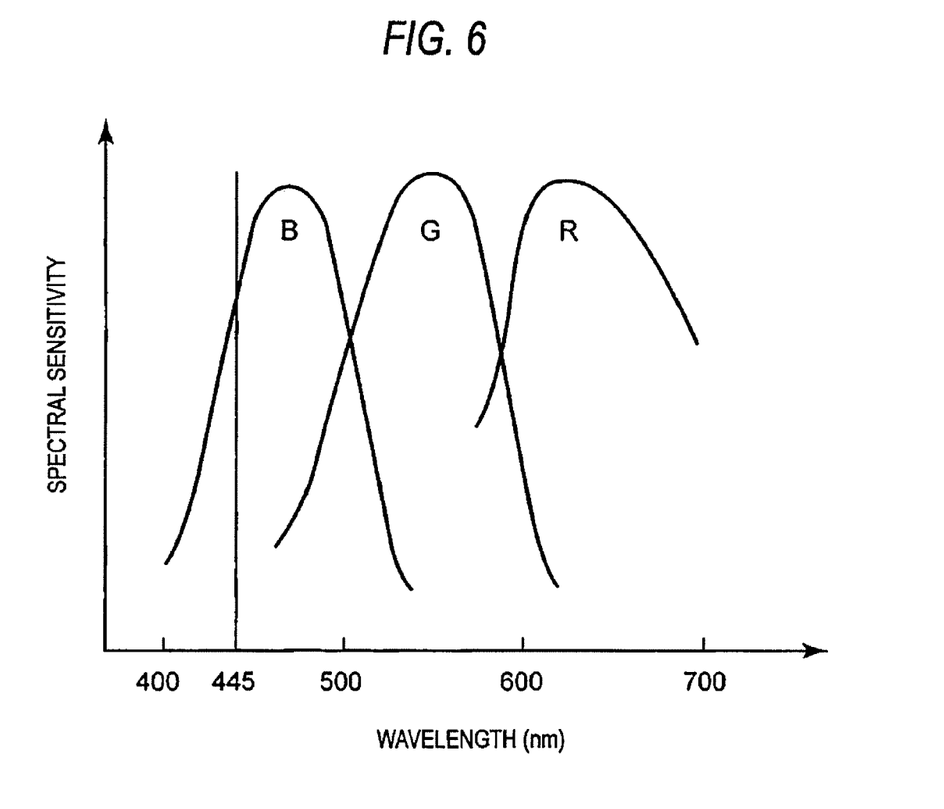
FIG. 6 is a graph showing a relationship between a wavelength and a spectral sensitivity characteristic of an imaging element.

FIG. 6 is a graph showing a relationship between the spectral sensitivity characteristic and the wavelength of the imaging element.

The imaging element 21 has the spectral sensitivity characteristics of B, G, and R with respect to the reflection light from the object. The laser light emitted from the blue laser light source 45 having a wavelength of 445 nm excites the fluorescent substance, and a part of the laser light transmits the fluorescent substance so as to be supplied as the blue component of the white illumination light. When the reflection light of the blue light is received by the imaging element 21, the spectral sensitivity characteristic of the imaging element 21 with respect to the B light has an area where a profile is steeply changed around the wavelength of 445 nm. Accordingly, when the spectral sensitivity characteristic of the imaging element 21 is slightly changed, the light receiving amount of the imaging element 21 with respect to the B light is changed. In addition, even when the light emission wavelength of the blue laser light source 45 is changed due to an individual difference or the like, the light receiving amount with respect to the B light is changed due to the same reason. For this reason, the tone of the captured image is changed due to the individual difference of the imaging element 21.

Accordingly, in the endoscope apparatus 100, the color is normally corrected on the captured image at all times by performing the calibration process as below.

In the endoscope apparatus 100, the endoscope 11 supported by the endoscope support unit 79 captures the image of the color chart 85 including a plurality of color patches having known chromaticity value by using the imaging element 21. The control section 93 obtains the chromaticity value of each of the plurality of color patches from the imaging signal of the color chart 85, and sets the chromaticity value as the measured chromaticity value. The control section 93 performs a calibration process which changes the contents of the color correction table 99 so that the measured chromaticity value of each of the color patches is equal to the known chromaticity value.

Therefore, according to the endoscope apparatus 100, the contents of the color correction table 99 are corrected so that the measured chromaticity value for each of the color patches obtained by the imaging element 21 is equal to the known chromaticity value, and the imaging signal of the captured image are close to the imaging signal of the original color.

Figure 7:
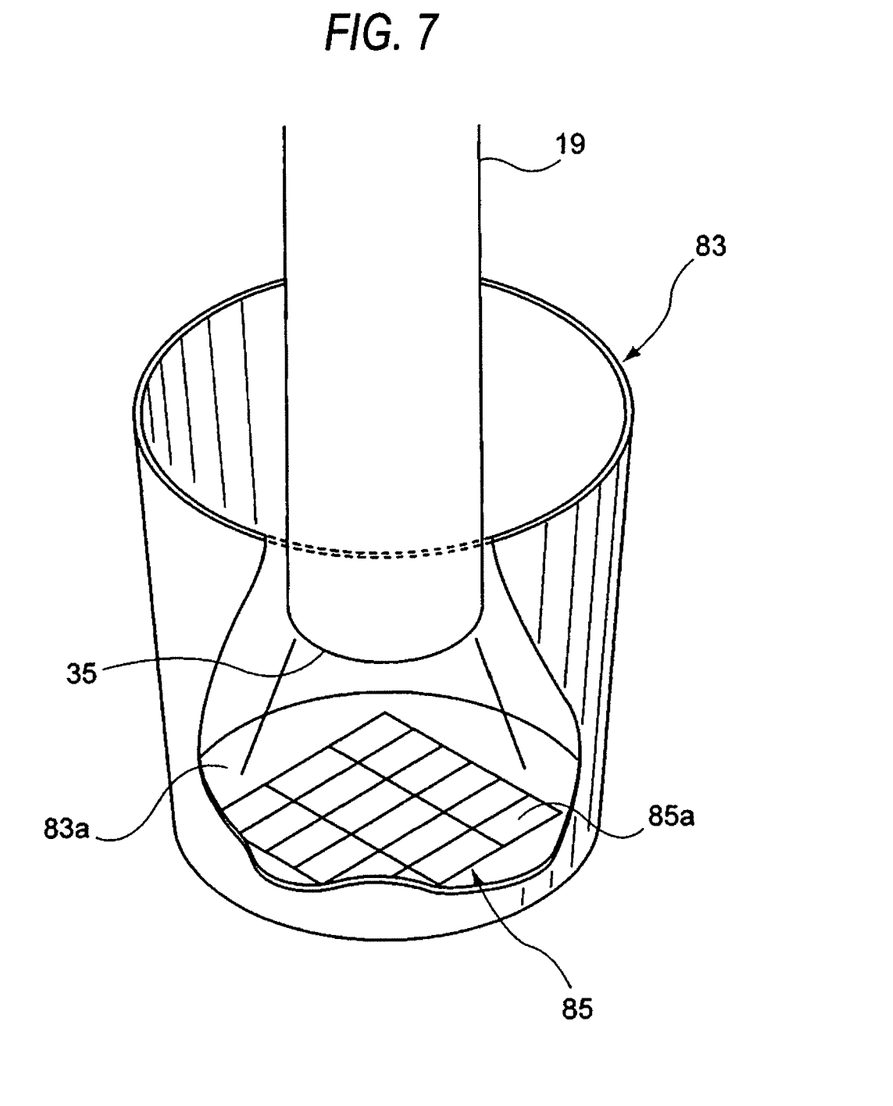
FIG. 7 is a perspective view of a bottomed cylindrical body which has a color chart provided in the bottom portion thereof and to which an endoscope front end portion is inserted.

As shown in FIG. 3, the color chart 85 is disposed at a bottom surface 83a of the bottomed cylindrical body 83 which accommodates the endoscope front end portion 35 in the inside of the inner peripheral surface at the lower portion of the front end portion 35 of the endoscope insertion unit 19 supported by the endoscope support unit 79. Here, FIG. 7 shows a perspective view of the bottomed cylindrical body which has the color chart provided at the bottom portion thereof and to which the endoscope front end portion is inserted. The calibration process is performed in the state where the drooped endoscope front end portion 35 is surrounded by the center portion of the bottomed cylindrical body 83.

That is, in the endoscope apparatus 100, the endoscope front end portion 35 takes a posture of facing downward at all times by suspending the endoscope 11 on the endoscope support unit 79. The color chart 85 is disposed so as to face the endoscope front end portion 35 taking a posture of facing downward. Accordingly, when a user just suspends the endoscope 11 on the endoscope support unit 79 without any intentional purpose, the endoscope front end portion 35 is disposed at a position facing the color chart 85. Accordingly, the preparation of the calibration process is completed just by an operation which is the quite the same as the operation in normal use, without any particular preparation for the calibration process. Then, when the endoscope front end portion 35 is inserted into the bottomed cylindrical body 83, it becomes a state where an influence caused by the disturbance of the external light hardly occurs during the calibration process. Likewise, in this configuration, without the help of a particular experiment environment, it is possible to perform the simple and highly precise calibration process by using the support state of the endoscope 11.

In the endoscope apparatus 100, various types of the color charts may be used.

Figure 8A:
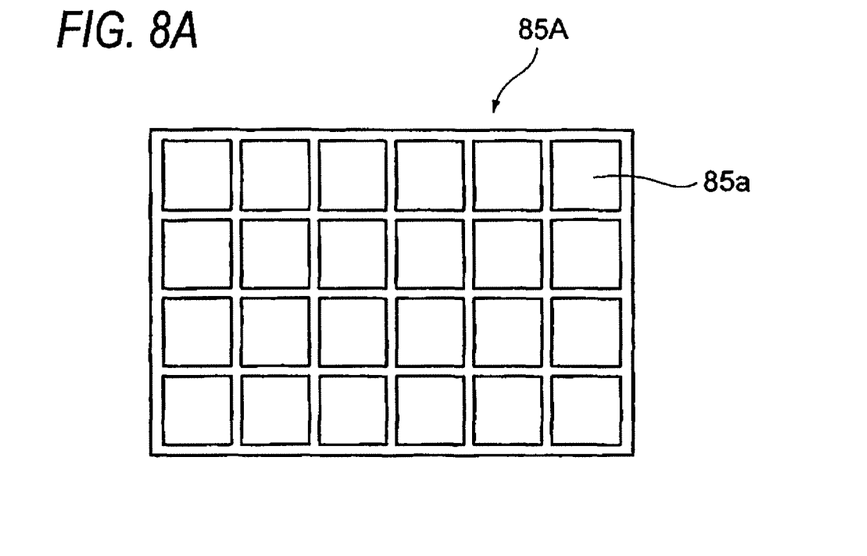
FIG. 8A is a plan view of the color chart having a lattice shape and formed by a plurality of color patches.
Figure 8B:
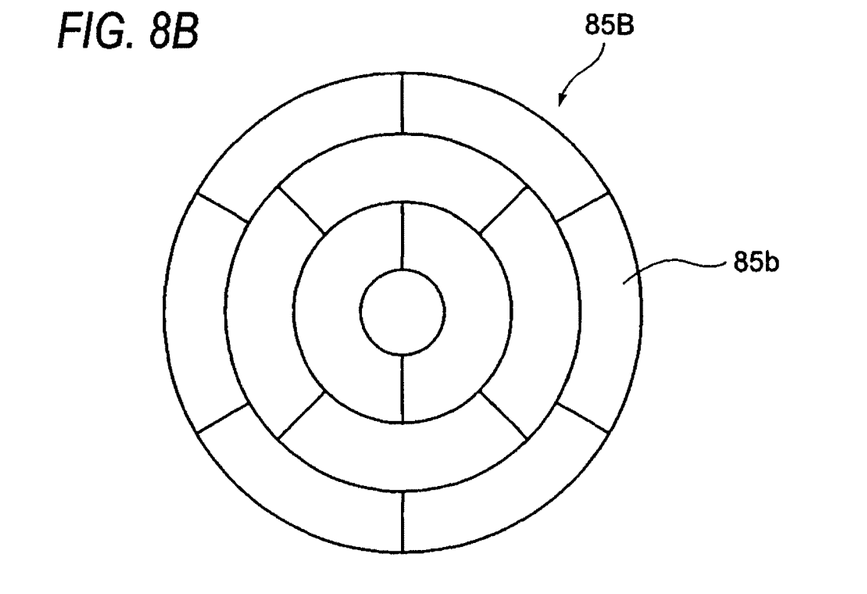
FIG. 8B is a plan view of the color chart having a circular shape and formed by a plurality of radial color patches divided in concentric circles.

FIG. 8A is a plan view of the color chart having a lattice shape and formed by a plurality of color patches, and FIG. 8B is a plan view of the color chart having a circular shape and formed by a plurality of radial color patches.

As shown in FIG. 8A, as the color chart, a color chart 85A formed by arranging a plurality of color patches (color tables) 85a in a lattice shape or a color chart 85B formed by arranging a plurality of circularly concentric divided color patches 85b in a radial shape may be used. When the image of the lattice-shaped color chart 85A is captured, for example, the color patches 85a at the corner portions may be omitted from the imaging screen. Regarding the concentrically divided color chart 85B, the color detection is stably performed at all times regardless of the imaging direction of the endoscope front end portion 35.

Next, the color correction procedure of the endoscope apparatus 100 will be described.

Figure 9:
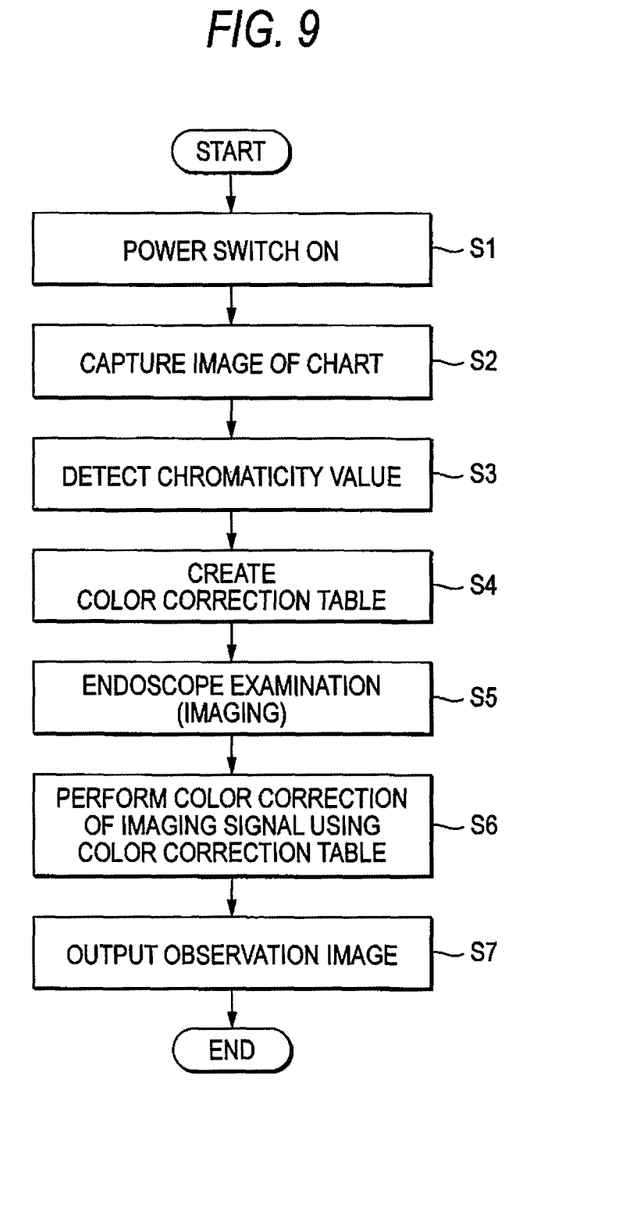
FIG. 9 is a flowchart of a color correcting procedure.

FIG. 9 shows the flowchart of the color correction procedure.

First, the power switch 97 of the endoscope 11 is turned on (S1). The control section 93 starts to capture the image of the color chart 85 at a start point as the timing of detecting the on state of the power switch 97 (S2). The calibration process is performed at the same time when the power switch 97 is turned on, thereby performing the simple and efficient calibration process.

After the image of the color chart 85 is captured, the chromaticity value of each of the plurality of color patches 85a is obtained from the imaging signal of the color chart 85, and is set as the measured chromaticity value (S3). The control section 93 performs the calibration process which changes the contents of the color correction table 99 so that the measured chromaticity value of each of the color patches 85a is equal to the existing chromaticity value (S4).

In the color correction process, generally, the color conversion matrix is used. The color conversion matrix is used to optimize the desired stimulus color value (target stimulus color value) when a plurality of reference colors R, G, and B in the input color space captured by the imaging element 21 are converted into the stimulus color spaces X, Y, and Z, and the like. The color conversion matrix is calculated at the final stage of the manufacture process of the endoscope apparatus 100, and the information on the calculated color conversion matrix is stored in the color correction LUT 99 mounted to the endoscope apparatus 100. In addition, after the conversion to the stimulus value spaces X, Y, and Z, the conversion to the Lab color space as the uniform color space may be performed, and the desired chromaticity value matching may be performed in the Lab color space.

In the calibration process of calculating the color conversion matrix, each matrix value ij is determined so that the stimulus value in accordance with the value of the RGB signal of the input color space obtained by photographing the reference color (color chart 85) by using the imaging element 21 is close to the stimulus value in accordance with the predetermined target color RGB signal value.

Then, after the calibration process, the calculation process is performed on the RGB signal input from the imaging element 21 by using the above-described color conversion matrix, so that the RGB signal obtained from the imaging element 21 is corrected to be close to the target color stimulus value. As a result, it is possible to perform the faithful color reproduction.

When the contents of the color correction table 99 are changed on the basis of the above-described contents, the image capturing operation is performed by the actual endoscope examination (S5). Then, the imaging signal obtained by the examination image capturing operation is subjected to the color correction by the color correction table 99 (S6), and the observation image based on the image signal subjected to the color correction is output to the display unit 15 (S7).

In addition, the target value (target color) set upon calculating the above-described color conversion matrix is mainly the colorimetric signal of the reference color, but may be set as the particular color actually observed by the endoscope 11, where the particular color may be the color of the surface layer of the mucous membrane of the biological tissue.

In addition, in the endoscope apparatus 100 for performing the observation or the examination of the inside of the body cavity, a PDD (Photodynamic Diagnosis) for tumor diagnosis may be performed in such a manner that a light sensitive material having tumor affinity and sensitive to a particular excitation light is injected into a living body in advance, laser light as the excitation light having a comparative weak output is emitted to a surface of a biological tissue, and fluoresce from a portion having an increased concentration of the light sensitive material in the involved site of a tumor such as a cancer is observed. In addition, in the endoscope apparatus 100, a PDT (Photodynamic Therapy) for tumor therapy of a tumor such as a cancer may be performed in such a manner that laser light having a comparatively strong output is emitted to a surface of a biological tissue.

In the laser light of 405 nm in the PDD, a medicine emits red fluorescence, and an affected site may be clearly observed. In addition, in the self-fluorescence, green fluorescence is emitted from the living body, and the light emission thereof is reduced in the affected site. When an unexpected color different from that of the normal observation image is displayed in order to easily detect such a variation, it is easy to determine the area or the existing location of the affected site.

As the purpose of the particular endoscope, it is possible to obtain image information which may be easily observed by performing a color correction while the color correction table 99 is set to a desired arbitrary value. For example, when a correction increases the luminance of the portion having green fluorescence and the portion having red fluorescence, the portions observed as vague green and red in the normal observation image are displayed as strong green and red. Such observation may be freely set of the color correction table 99 through the emphasis process in accordance with the purpose of the observation. In the color chart 85 which is suitable for the above-described color conversion and is used as a particular color chart, for example, a plurality of color patches 85a exists between red and green, and a difference of delicate color is stipulated. On the contrary, the blue color patch 85a does not exist.

As described above, various types may be selectively used as the color chart 85 used in the endoscope apparatus 100 in accordance with the observation purpose. The respective color charts may be the arrangement patterns of different colors. In order to identify each of the plurality of types of color charts, for example, the type information of the color chart shown in Table 1 may be stored in advance in the storage section 95 (refer to FIG. 1), and may be appropriately used for reference.

TABLE 1

| CODE | TYPE | CHART PATTERN |
|---|---|---|
| 1 | UPPER DIGESTIVE TRACT EXAMINATION CHART | 4 × 6 SQUARE PATCH |
| 2 | LOWER DIGESTIVE TRACT EXAMINATION CHART | 3 × 3 SQUARE PATCH |
| 3 | BRONCHIAL EXAMINATION CHART | 4 × 4 SQUARE PATCH |
| 4 | PDD EXAMINATION CHART | 12 CIRCLE PATCH |

That is, according to the type information of the color chart shown in Table 1, the color chart having a code number of 1 is used to examine an upper digestive tract, and a plurality of types of color patches having delicate colors is prepared for the mucous membrane of the biological tissue. In the upper digestive tract, a throat, a stomach, and a duodenum correspond to an examination target. Since there is a case where it is important to identify the color of infection or tumor, in order to accurately identify the color, many color samples (color patches) around the color are included in the color chart.

In these color charts, it is possible to further improve the convenience thereof when identification information is provided on a display surface of the color chart.

Figure 10:
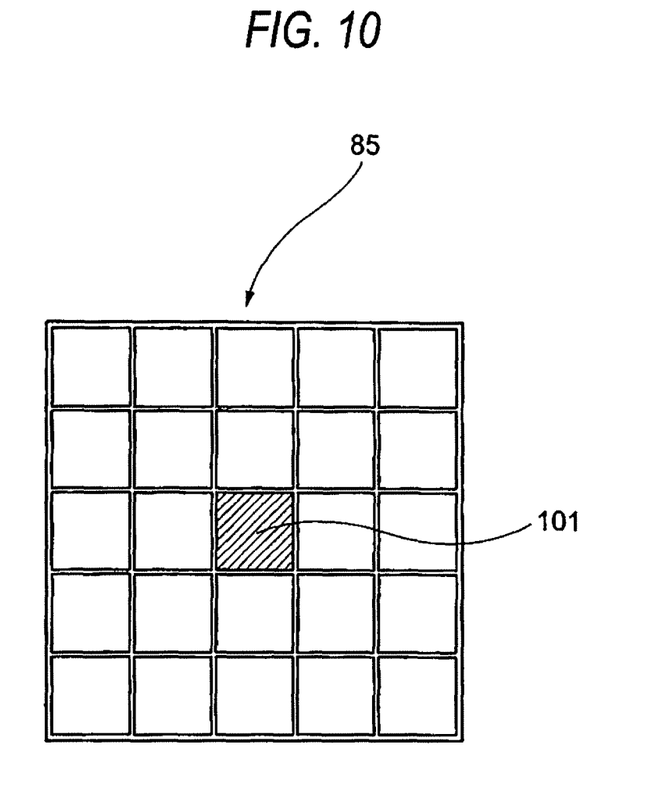
FIG. 10 is a plan view of a color chart having identification information added thereto.

FIG. 10 is a plan view of a color chart having identification information added thereto. In the color chart 85, identification information 101 is provided at a certain position within the chart. As the identification information, a general identification means such as a one-dimensional barcode and a two-dimensional QR code may be used. In addition, in addition to the barcode, various signs, arrangement of signs, a character string such as a numeral string, or the type or characteristic of the treatment tool for the endoscope may be used. If the extraction and recognition (analysis) may be performed by using the image capturing process, various types may be used.

In the color chart 85, first, the image of the color chart 85 is captured by the imaging element 21, the identification information 101 is recognized from the captured image, and the type (code) of the color chart 85 is determined. In accordance with the determined code, the calibration process is performed by using an algorithm corresponding to the determined color chart on the basis of the type information shown in Table 1. The calibration program of the algorithm corresponding to each color chart is stored in advance in the storage section 95, and several programs are selectively read out so as to be executed by the control section 93. Accordingly, it is possible to automatically perform the calibration process by using the different algorithms in accordance with the types of the light sources for PDD and PDT.

Next, an example will be described which has a configuration in which the imaging environment is hardly influenced by the external light by shielding light to the portion provided with the color chart.

Figure 11A:
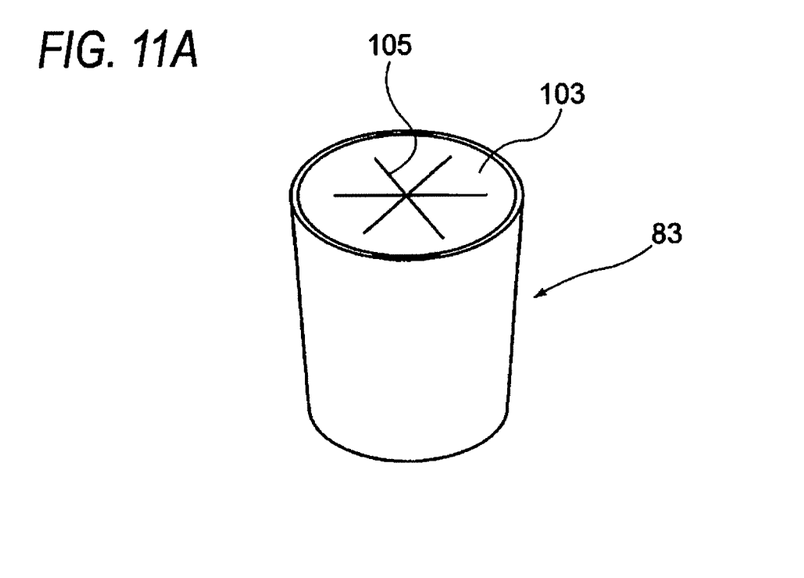
FIG. 11A is a perspective view of a bottomed cylindrical body of which the upper portion is closed by a cover having an insertion hole.
Figure 11B:
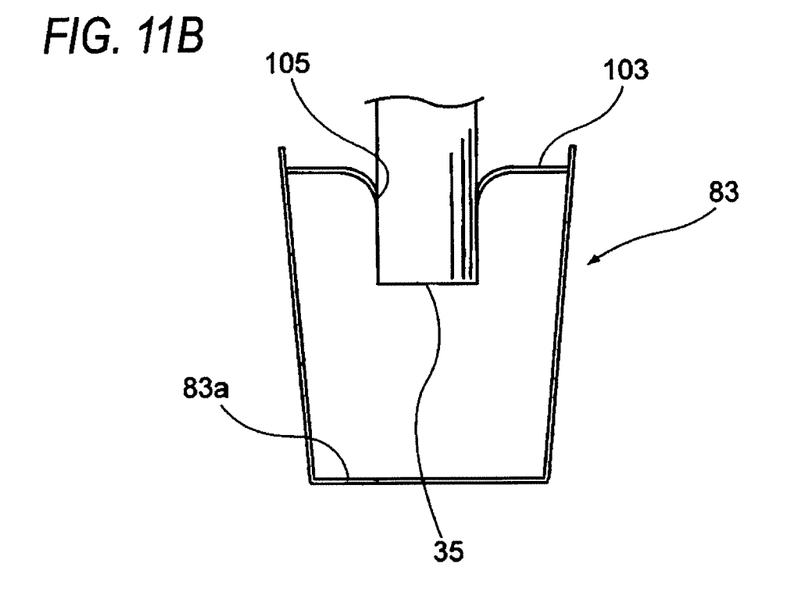
FIG. 11B is a cross-sectional view of FIG. 11A.

FIG. 11A is a perspective view of a bottomed cylindrical body of which the upper portion is closed by a cover having an insertion hole, and FIG. 11B is a cross-sectional view thereof.

The bottomed cylindrical body 83 includes a cover 103 which covers the upper portion thereof and has a light shielding property. The cover 103 is provided with an insertion hole 105 which allows the endoscope front end portion 35 to be inserted into the insertion hole 105. With such a configuration, the drooped endoscope front end portion 35 is supported to the endoscope support unit 79, and is inserted into the insertion hole 105 of the cover 103 provided in the bottomed cylindrical body 83 so as to be positioned and supported at the center portion of the diameter of the bottomed cylindrical body 83. In addition, since the endoscope front end portion 35 may be stored into the light shielding space by the cover 103, it is possible to perform the calibration process which is hardly influenced by the disturbance caused by the external light.

In addition, since the endoscope front end portion 35 is supported by the cover 103, it is possible to reliably prevent the endoscope front end portion 35 from being shaken during the movement or the like of the cart unit 77 (refer to FIG. 3), and to protect the endoscope front end portion 35 mounted with a precise electronic device such as an imaging element.

Further, in the endoscope apparatus 100 with the above-described configuration 100, the timing upon turning on the power switch 97 is used as the start point, but for example, the calibration process may be performed by setting the timing upon detecting the exchange of the fluorescent substance 57 as the start point. According to such a configuration, it is possible to perform the calibration process corresponding to the spectrum for each product of the newly exchanged fluorescent substance 57, and to obtain a captured image having a satisfactory color balance at all times.

Furthermore, in the case where the light source unit 47 supplies laser light (light having a narrow bandwidth of a wavelength of 405 nm) having a wavelength shorter than that of the blue laser light for forming the white light in order to observe the image of the blood vessel of the surface layer of the tissue, the illumination light synthesized with the white light has a bluish tone due to the existence of the particular light. Even in this case, by creating the color correction table 99 used to perform the color correction for suppressing the bluish color, the color correction suitable for the tone of the illumination light is performed, and the captured image having appropriate chromaticity value may be obtained at all times.

Moreover, whenever the calibration for the color adjustment is performed, the timing of performing the calibration is different for each user of the endoscope apparatus 100. In addition, at the time of actual operation, when the calibration is performed, a mechanism for performing the calibration needs to be prepared, which is troublesome work. On the contrary, according to the present endoscope apparatus 100, even when an operation almost the same as that of the normal case is performed, the calibration process is automatically performed, and the imaging signal having a satisfactory color balance may be obtained at all times. For this reason, it is possible to prevent the calibration process from being used and continued in the state where the color balance of the endoscope 11 is collapsed.

Likewise, the present invention is not limited to the above-described embodiment, but corrections and applications thereof may be made by the person skilled in the art on the basis of the description of the specification and the known technology, and those are included in the scope required to be protected.

As described above, the present specification discloses the following items.

(1) An endoscope apparatus including: an endoscope which includes an imaging optical system having an imaging element and an illumination optical system having an illumination window, the optical systems being provided at a front end of an endoscope insertion unit inserted into a body cavity; and a control means which includes a light source unit connected to the endoscope and supplying at least excitation light to the illumination optical system so as to emit light from a fluorescent substance, and an image processing section correcting an image signal output from the imaging element on the basis of a predetermined color correction table and outputting the result thereof, wherein the control means performs a calibration process in such a manner that an image of a color chart having a plurality of color patches with known chromaticity values is captured by the imaging element, chromaticity for each of the plurality of color patches is obtained from an imaging signal of the color chart so as to be used as a measured chromaticity value, and the contents of the color correction table are changed so that the measured chromaticity value of each of the color patches is equal to the known chromaticity value.

According to the endoscope apparatus, the calibration process of the contents of the color correction table is performed so that the measured chromaticity value for the color patch obtained by the imaging element is equal to the known chromaticity value, and the imaging signal of the captured image may be close to the imaging signal value of the original color.

(2) The endoscope apparatus according to (1), wherein the control means performs the calibration process at a start point as the timing of detecting an on state of a power switch.

According to the endoscope apparatus, for example, the calibration process is performed at the same time when the power switch is turned on immediately before the use of the endoscope apparatus, and hence the calibration process may be performed simply and efficiently.

(3) The endoscope apparatus according to (1), wherein the control means performs the calibration process at a start point as the timing of detecting an exchange of the fluorescent substance.

According to the endoscope apparatus, it is possible to perform the calibration process corresponding to the excitation/light emission spectrum for each product of the newly exchanged fluorescent substance.

(4) The endoscope apparatus according to (1), wherein the illumination optical system includes a plurality of fluorescent substances which is disposed at different positions of the front end of the endoscope insertion unit, and a light guiding member which guides the excitation light from the light source unit to the fluorescent substance.

According to the endoscope apparatus, it is difficult to form a shade on an object illuminated by the illumination light.

(5) The endoscope apparatus according to (1), wherein the excitation light generated from the light source unit is blue laser light, the fluorescent substance emits light by the blue laser light as the excitation light, and white light is formed by the light emitted from the fluorescent substance and the blue laser light.

According to the endoscope apparatus, since the white light is formed by the fluorescent substance and the blue laser light, it is possible to obtain the white light which has high efficiency and high intensity. It is easy to correct the white light even when the spectral characteristic of the illumination light is changed due to a variation in time of the fluorescent substance or a difference in the wavelength of the laser light.

(6) The endoscope apparatus according to (5), wherein the light source unit supplies laser light, which has a property of passing through the fluorescent substance and has a wavelength shorter than that of the blue laser light, to the illumination optical system.

According to the endoscope apparatus, even in the case where laser light having a wavelength shorter than that of the blue laser light for forming the white light in order to observe the image of the blood vessel of the surface layer of the tissue (the case where the captured image is bluish), it is possible to obtain the captured image having appropriate chromaticity at all times by creating the color correction table for each laser light.

(7) The endoscope apparatus according to (1), further including: an endoscope support unit which supports the endoscope in a suspended state, wherein the color chart is disposed so as to face the front end of the endoscope insertion unit which is supported by the endoscope support unit in a drooped state.

According to the endoscope apparatus, since the endoscope is supported by the endoscope support unit, the front end of the endoscope insertion unit takes a posture of facing downward at all times. Since the color chart is disposed to face the front end, it is possible to perform the simple and highly precise calibration process by using the support state of the endoscope, without the help of a particular experiment environment.

(8) The endoscope apparatus according to (7), wherein the endoscope support unit is installed in a cart unit which is mounted with a peripheral device of the endoscope.

According to the endoscope apparatus, the peripheral devices such as the processor, the light source device, the display unit, and the input unit necessary for the image capturing operation of the endoscope are all accommodated in the cart unit. Since the endoscope support unit is installed in the cart unit, it is possible to perform the image capturing operation with the calibration process while the endoscope is supported.

(9) The endoscope apparatus according to (7), wherein the color chart is disposed at a bottom surface of the bottomed cylindrical body which accommodates the endoscope insertion unit, supported by the endoscope support unit, in the inside of the inner peripheral surface thereof.

According to the endoscope apparatus, the front end of the endoscope supported by the endoscope support unit in a drooped state is inserted into the center portion of the bottomed cylinder in a surrounded state. Therefore, it is possible to perform the calibration process which is hardly influenced by the disturbance caused by the external light.

(10) The endoscope apparatus according to (9), further including: a cover which covers the upper portion of the bottomed cylindrical body, and has a light shielding property, wherein an insertion hole is perforated in the cover so as to allow the front end of the endoscope insertion unit to be inserted thereinto.

According to the endoscope apparatus, the front end of the endoscope supported by the endoscope support unit in a drooped state is inserted into the insertion hole of the cover provided in the bottomed cylinder, and is positioned and supported at the center portion thereof. In addition, since the front end is covered by the cover, it is possible to perform the calibration process which is hardly influenced by the disturbance caused by the external light.

(11) The endoscope apparatus according to (1), wherein the color chart includes an identification means for identifying the color chart.

According to the endoscope apparatus, the type of the color chart is determined by the identification means, and a different calibration process may be performed for each type.

What is claimed is:

1. An endoscope apparatus comprising:
    an endoscope which includes an imaging optical system comprising an imaging element and an illumination optical system comprising an illumination window, the optical systems being provided at a front end of an endoscope insertion unit inserted into a body cavity;
    a control unit which includes a light source unit connected to the endoscope and supplying at least excitation light to the illumination optical system so as to emit light from a fluorescent substance, and an image processing section correcting an image signal output from the imaging element on a basis of a predetermined color correction table and outputting a result thereof;
    an endoscope support unit which supports the endoscope in a suspended state;
    a bottomed cylindrical body which is supported by the endoscope support unit; and
    a cover which covers an upper portion of the bottomed cylindrical body, and includes a light shielding property,
    wherein the endoscope apparatus further comprises a storing unit that stores the color correction table,
    wherein the control unit performs a calibration process that an image of a color chart comprising a plurality of color patches with known chromaticity values is captured by the imaging element, chromaticity for the plurality of color patches is obtained from an imaging signal of the color chart so as to be used as a measured chromaticity value, and contents of the color correction table stored in the storing unit are changed so that the measured chromaticity value of the color patches is equal to the known chromaticity value,
    wherein the color chart is disposed so as to face a front end of the endoscope insertion unit which is supported by the endoscope support unit in a drooped state,
    wherein the color chart is disposed at a bottom surface of the bottomed cylindrical body which accommodates the front end of the endoscope insertion unit in an inside of an inner peripheral surface thereof, and
    wherein an insertion hole is perforated in the cover so as to allow the front end of the endoscope insertion unit to be inserted thereinto.

2. The endoscope apparatus according to claim 1, wherein the control unit performs the calibration process at a start point as a timing of detecting an on state of turning on a power switch.

3. The endoscope apparatus according to claim 1, wherein the control unit performs the calibration process at a start point as a timing of detecting an exchange of the fluorescent substance.

4. The endoscope apparatus according to claim 1, wherein the illumination optical system includes a plurality of fluorescent substances which is disposed at different positions of a front end of the endoscope insertion unit, and a light guiding member which guides the excitation light from the light source unit to the fluorescent substance.

5. The endoscope apparatus according to claim 1, wherein the excitation light generated from the light source unit comprises a blue laser light, the fluorescent substance emits light by the blue laser light as the excitation light, and white light is formed by the light emitted from the fluorescent substance and the blue laser light.

6. The endoscope apparatus according to claim 5, wherein the light source unit supplies laser light, which includes a property of passing through the fluorescent substance and includes a wavelength shorter than that of the blue laser light, to the illumination optical system.

7. The endoscope apparatus according to claim 1, wherein the endoscope support unit is installed in a cart unit which is mounted with a peripheral device of the endoscope.

8. The endoscope apparatus according to claim 1, wherein the color chart is formed by arranging the plurality of color patches in a lattice shape.

9. The endoscope apparatus according to claim 1, wherein the color chart is formed by arranging a plurality of circularly concentric divided color patches in a radial shape.

10. The endoscope apparatus according to claim 1, wherein the insertion hole is configured so as to secure the front end of the endoscope insertion unit.

11. The endoscope apparatus according to claim 1, wherein the color chart includes an identification section for identifying the color chart.

12. An endoscope apparatus comprising:
    an endoscope which includes an imaging optical system comprising an imaging element and an illumination optical system comprising an illumination window, the optical systems being provided at a front end of an endoscope insertion unit inserted into a body cavity;
    a control unit which includes a light source unit connected to the endoscope and supplying excitation light to the illumination optical system so as to emit light from a fluorescent substance, and an image processing section correcting an image signal output from the imaging element on a basis of a predetermined color correction table and outputting a result thereof;
    an endoscope support unit which supports the endoscope in a suspended state; and
    a cover which covers an upper portion of the bottomed cylindrical body, and includes a light shielding property,
    wherein the control unit performs a calibration process that an image of a color chart comprising a plurality of color patches with known chromaticity values is captured by the imaging element, chromaticity for the plurality of color patches is obtained from an imaging signal of the color chart so as to be used as a measured chromaticity value, and contents of the color correction table are changed so that the measured chromaticity value of the color patches is equal to the known chromaticity value, wherein the color chart is disposed so as to face a front end of the endoscope insertion unit which is supported by the endoscope support unit in a drooped state, wherein an insertion hole is perforated in the cover so as to allow the front end of the endoscope insertion unit to be inserted thereinto.

* * * * *